United States Patent [19]
Randall et al.

[11] Patent Number: 5,945,090
[45] Date of Patent: Aug. 31, 1999

[54] SUNSCREEN PREPARATION

[75] Inventors: William B. Randall, Carlsbad; Cary L. Prida, San Diego, both of Calif.

[73] Assignee: Randall Products International, Carlsbad, Calif.

[21] Appl. No.: 08/927,471

[22] Filed: Sep. 11, 1997

[51] Int. Cl.⁶ .............................. A61K 7/42; A61K 31/74; A61K 35/78; A61K 7/00
[52] U.S. Cl. ........................... 424/59; 424/60; 424/78.02; 424/78.03; 424/195.1; 424/400; 424/401
[58] Field of Search ................................. 424/89, 60, 400, 424/401, 195.1, 78.02, 78.03

[56] References Cited

U.S. PATENT DOCUMENTS

| | | | |
|---|---|---|---|
| 5,256,404 | 10/1993 | Martino et al. | 424/59 |
| 5,505,935 | 4/1996 | Guerrero et al. | 424/59 |
| 5,741,497 | 4/1998 | Guerrero et al. | 424/401 |

*Primary Examiner*—Shelley A. Dodson
*Attorney, Agent, or Firm*—George J. Netter

[57] ABSTRACT

A high-SPF composition is provided which is quick drying, waterproof and anti-perspiration penetrating which after application rapidly is very dry and soft to the touch comprising a sunscreen with both UVA and UVB components, an algae extract and aloe vera, and tapioca powder. In a further example, an enhancing agent consisting of styrene acrylates copolymer is added.

4 Claims, No Drawings

SUNSCREEN PREPARATION

BACKGROUND

1. Background of the Invention

The present invention relates generally to a sunscreen preparation of modifiable high screening capability and, more particularly, to such a preparation which is quick drying after topical application to the skin and does not have either tacky or slippery consistency but instead quickly leaves the skin dry, smooth and soft.

2. Description of Related Art

The medical profession has been stating for many years with increasing emphasis that exposure of the human skin to the rays of the sun is dangerous and tends to produce skin cancer if continued. This dangerous condition is exacerbated in certain types of individuals who are more susceptible to skin damage from solar radiation than others and, accordingly, it has been suggested that when individuals are to be in the sunlight for any significant period of time, that they not only wear proper clothing to block out the sun's rays from major skin surfaces, but also to protect exposed parts of the body (e.g., the face, neck, hands and arms) by topical application of a cream or other preparation that contains a block or screening material to reduce the amount of radiation reaching the skin.

In sporting activities such as golf, tennis, and hiking, for example, that take place in open air where the player is exposed to the direct rays of the sun, this requirement for protection from the sun rays is increased. For example, a typical round of golf will last approximately four hours during which time the individual, on a clear day, may be directly exposed to the sun's rays at least 70–80 percent of that time.

Typically, nowadays individuals engaging in sports apply a sun preparation of either the sunblock or sunscreen category at least to the hands, face and neck since these areas are preferably not covered by clothing during participation in many sports. However, common complaints concerning such preparations are that they do not dry quickly and therefore leave the hands slippery for an extended period of time which impedes proper gripping or other utilization of a sporting implement such as a golf club or tennis racket. Still further, other sun products are frequently objected to as being tacky such that gripping of a sport implement is unpleasant or difficult which disturbs concentration of someone engaged in sport. At the least, these prior sun preparations interfere with the concentration ability of the one engaging in the sport which destroys a certain amount of competence from that source alone. There is also the good possibility that if the sunscreen product results in slippery or tacky hands, that the individual will use nothing rather than the offending product thereby leaving the skin of the individual at risk.

It is therefore desirable to provide a sun preparation particularly for topical application to the skin of a sports enthusiast which quickly dries and does not have an unpleasant to the touch feel such as slipperiness, tackiness or other unpleasant tactile sensation. Such a quick drying preparation will therefore enhance proper handling of sports implements such as golf clubs, tennis rackets. In addition, there are certain individuals who have a tendency when normally engaged in a sports activity to quickly develop wetness of the palms and fingers and would, therefore, benefit from a sun preparation that would reduce substantially to the zero point this tendency toward hand perspiration.

Additionally, it is desirable to achieve a broader frequency spectrum of protection and this typically requires two materials referred to as UVA and UVB sunscreen agents where a UVA agent is most effective for the 320–400 nm wavelengths and a UVB agent more readily absorbs ultraviolet rays in the 250–320 nm range.

SUMMARY OF THE INVENTION

In accordance with the practice of the present invention, there is provided a modifiable high SPF sunscreen product which is quick drying after topical application leaving a soft dry feel that is neither slippery nor tacky, includes at least a UVA or UVB material, an alcohol carrier, and possesses both waterproof and anti-perspiration penetrating characteristics. The preparation can be provided in strength ranges from SPF4 to SPF20.

According to a preferred embodiment, there is provided a sunscreen preparation quick drying, soft to the touch, non-slippery, non-tacky, waterproof, and resistant to penetration by perspiration, comprising by weight for an SPF8 formulation:

(a) about 1 to about 9.57 percent of a sunscreen material containing at least one UVA and one UVB sunscreen component;

(b) about 1 to about 11.26 percent of a solvent such as alcohol;

(c) about 1 to about 58.73 percent of water;

(d) about 1 to about 16.89 percent of tapioca flour;

(e) about 1 to about 1.13 percent of algae extract and aloe vera gel;

(f) about 1 to about 2.42 percent sunscreen enhancer and waterproofing component.

In addition, the described sunscreen composition may include by weight:

(g) about 0 to 0.35 percent of a thickener and waterproofing agent;

(h) about 0 to 0.50 percent of pantothenic acid;

(i) about 0 to 0.10 percent of chelating agent;

(j) about 0 to 0.35 percent of a neutralizer;

(k) about 0 to 1.00 percent of a fatty acid binder;

(l) about 0 to 2.00 percent of a non-oily emollient;

(m) about 0 to 2.0 percent skin conditioning ester;

(n) about 0 to 0.5 percent vitamin E acetate;

(o) about 0 to 1.5 percent silicone;

(p) about 0 to 1.5 percent silicone emulsifier;

(q) about 0 to 0.04 percent anti-oxidant;

(r) about 0 to 0.5 percent emulsifier;

(s) about 0 to 0.5 percent fragrance;

(t) about 0 to 1.8 percent sunscreen enhancer and waterproofing component.

DESCRIPTION OF PREFERRED EMBODIMENTS

The invention relates generally to a sunscreen formulation for topical application to human skin to prevent burning and other damage that can be caused by harmful ultraviolet radiation and which formulation is quick drying, soft to the touch, waterproof, non-greasy, non-tacky and prevents perspiration passing therethrough.

Component percentages set forth herein are by weight in each case.

Sunscreen Agents

The specific sunscreen components used in the first described example are octyl methoxycinnamate sold under the trade designation PARSOL MCX by Roche and benzophenone-3 sold under the trade designation UVINUL M-40 by B.A.S.F., which components are utilized in a mixture. The amount of sunscreen components used will depend upon the desired ultimate SPF figure as specifically called out in the Examples of the invention given later herein.

In the second described Example, the additional sunscreen components used are Parsol 1789 (butyl methoxydibenzoylmethane) and Dermablock (octyl salicylate).

Various suitable sunscreen materials for advantageous employment in this invention are to be found in, "A Survey of Ultraviolet Absorbers in Commercially Available Sun Products", by Roelandts et al., *International Journal of Dermatology*, Vol. 22, pages 247–255 (May, 1985).

MOISTURE LOSS RETAINING AND SOFTENING AGENT

The surprising softening effect obtained in use of the described sunscreen preparation is the synergistic result of combining selected marine algae (*macrocystis spyriferae*) with the inner gel of *aloe barbadensis* Miller, and finely ground tapioca flour.

More particularly, a combination of algae extract and aloe vera gel is available on the market having sugar oligosaccharides in a form which in the final formulation produces a moisturizing aspect. The product is sold under the registered trademark Actisea by Active Organics.

Also, the algae extract and aloe vera gel work synergistically to provide a biomolecular hygroscopic moisture barrier which retards transepidermal moisture loss.

The tapioca is ground to a particle size of 20 microns and can be used in either a powdered product, or in an emulsion system which is the preferred form here. The powder provides a dry powdery soft skin feel in either powders or emulsions. An excellent powder form of tapioca is sold under the trade designation Tapioca Pure by National Starch and Chemical Company of Bridgewater, N.J.

Enhancing Agent

A copolymer ingredient styrene acrylates copolymer enhances the effectiveness of other ingredients. This polymer is structurally a bead with a core which in emulsion form is filled with water. On application of sunscreen formulation to the skin and drying of the sunscreen film, the water irreversibly migrates from the center, leaving an air-filled center. The entrapped air acts as an efficient scattering center to increase the path length of radiation passing through the sunscreen film resulting in more efficient use of the sunscreen agent. An excellent source of this copolymer for present purposes is marketed under the brand name ACUDYNE-290 by Rohm Haas.

Optional Ingredients

Conventional thickener and waterproofing agent can be included in suitable amounts.

A precursor for vitamin B5 such as Dex Panthenol provides a deep penetrating moisturizing action, and improves skin smoothness. Vitamin E in acetate form improves skin smoothness and aids in prevention of free radical damage caused by the sun.

The emollient and solvent system preferably includes a specially denatured ethyl alcohol referenced in "Alcohol S.D. 39 C".

Typically cosmetic additives such as selected fragrance and coloring agents are also included.

Formulation Form

Although the invention can be employed in a variety of forms, the preferable form is that of a flowable liquid in view of ease of application and which will dry quickly.

EXAMPLES

Example 1: SPF8 Sunscreen Emulsion
Procedure in Mixing

Sprinkle the thickener and waterproofing ingredient into the deionized water in a suitable container and mix 1–2 hours until completely lump-free. Add the remainder of the Part A ingredients, one at a time, and mix well. This is termed the "water phase".

In a separate container, weigh the first four (4) components of Part B, heating to 45–50° C. Now, add the second sunscreen material (UVINOL M-40) to the heated ingredients, mixing thoroughly to form what is termed the "oil phase". Add all the remaining ingredients of Part B except the alcohol to the oil phase. Then, pour specially denatured alcohol at about 39° C. pour into the oil phase and mix.

The oil phase is now slowly poured into the water phase and mixed for about 20 minutes following which the sunscreen enhancer (Acudyne) is added while continuing mixing.

With the batch just described at a temperature not higher than 30° C., the tapioca flour is added and mixed for at least 30 minutes until the final formulation is smooth.

| Ingredients | Percent by Weight |
| --- | --- |
| PART A | |
| Deionized Water | 52.16 |
| Thickener Waterproofing Agent: PEMULEN TR-1 acrylates/C10–30, alkyl acrylate cross-polymer. | 0.35 |
| Aloe Vera/algae extract | 1.00 |
| Pantothenic acid | 0.50 |
| Preservative: propylene glycol, DMDM hydantoin, methylparaben, propyl-paraben | 0.70 |
| Chelating agent: tetrasodium EDTA | 0.10 |
| Triethanolamine neutralizer | 0.35 |
| PART B | |
| Isostearic acid | 1.00 |
| Emollient non-oily C12–15 alkyl benzoate | 2.00 |
| Skin conditioning ester propylene glycol dicaprylate/dicaprate | 2.00 |
| Sunscreen: UVB octyl methoxycinnamate | 7.50 |
| Sunscreen: B enzophenone-3 | 1.00 |
| Vitamin E acetate | 0.50 |
| Silicone | 1.50 |
| Silicone emulsifier | 1.50 |
| Antioxidant | 0.04 |
| Emulsifier | 0.50 |
| Fragrance | 0.50 |
| Alcohol, specially denatured | 10.00 |

| Ingredients | Percent by Weight |
|---|---|
| Tapioca flour | 15.00 |
| Sunscreen enhancer denatured | 1.80 |

Example 2: SPF 8 Sunscreen Emulsion

Procedure in Mixing

Sprinkle the thickener and waterproofing ingredient Pemulen TR-1 into the deionized water (DI) and mix 1–2 hours until lump-free. Add remainder of Part A ingredients, one at a time, and mix to form the "water phase".

Pre-mix Nayad SGM in DI water, allowing 30 minutes to completely dissolve, and add to the water phase. Also, pre-mix triethanolamine (TEA) in DI water and add to water phase.

In another container, weigh the first four (4) ingredients of Part B and heat to 45–50° C. Add the sunscreen ingredient Parsol 1789 to the batch and mix thoroughly to form the "oil phase". Add ingredients 17–23 of Part B to the oil phase. Now add the SD alcohol 39C while mixing. Lastly, mix in S.F. 1328. Lastly, mix in S.F. 1328.

Slowly pour the oil phase into the water phase mix for about 20 minutes and then add the sunscreen enhancer Acudyne 290 while continuing mixing.

With the batch at a temperature well below 30° C. add Sungen. The final step consists of slowly adding the tapioca flour and mixing for at least 30 minutes with batch temperature at not more than 28° C.

| Ingredient | % By Weight |
|---|---|
| PART A | |
| Deionized water | 47.923 |
| Pemulen TR-1, Acrylates/ C10–30 Alkyl Acrylate Crosspolymer | 0.37 |
| Actisea 50, Aloe Barbadensis Gel, Algae Extract | 1.00 |
| Dex Panthenol | 0.50 |
| Sequestrine 30A, Tetrasodium EDTA | 0.10 |
| DI Water | 0.50 |
| Nayad SGM | 0.007 |
| DI Water | 0.30 |
| Uniphen P-23, Phenoxyethanol, methylparaben, Ethylparaben, Propylparaben, Butylparaben | 0.70 |
| DI | 0.70 |
| Triethanolamine 99% | 0.40 |
| PART B | |
| Finsolv TN (C12–15 Alkyl Benzoate) | 2.00 |
| Liponate TDS (Tridecyl Stearate) | 2.00 |
| Isostearic Acid | 1.00 |
| Parsol MCX, Octyl Methoxycinnamaate | 7.50 |
| Dermablock (Octyl Salicylate) | 3.00 |
| Parsol 1789, Butyl Methoxy-dibenzoylmethane | 1.50 |
| Vitamin E Acetate, Tocopheryl Acetate | 0.50 |
| Stearyl Glycyrrhetinate | 0.05 |
| Pyridoxine DP, Pyridoxine Dipalmitaate | 0.05 |
| BV-OSC, Ascorbyl Tetra-isopalmitate | 0.20 |
| Polyoprepolymer-2, PPG/SMDI Copolymer | 0.50 |
| Liposorb 0–20, Polysorbate 80 | 0.50 |
| D.C. 345, Cyclomethicone | 1.50 |
| S.F. 1328 or D.C. 3225C, Cyclomethicone, Dimethicone Copolyol | 1.50 |
| S.D. Alcohol 39C | 10.00 |
| Acudyne 290, Styrene Acrylates Copolymer | 1.75 |
| Sungen, Hydrolyzed Soy Protein, Shea Butter Unsaponifiables | 0.50 |
| Tapioca Flour | 14.50 |

Although the invention has been described in connection with certain preferred examples, it is to be understood that those skilled in the appertaining arts may make changes without departing from the scope of the described invention or the appended claims.

What is claimed is:

1. A quick-drying, waterproof, non-slip sunscreen composition, comprising:

(a) from about 1% to about 41% by weight of at least one UVA and one UVB component;

(b) from about 1% to about 6% by weight of styrene acrylates copolymer;

(c) from about 1% by weight to about 49% by weight of tapioca powder; and (d) from about 1% by weight to about 4% by weight of *macrocystis spyriferae* algae extract and *naloe barbadensis* Miller.

2. The composition of claim 1, in which there is further provided from about 0 to about 29% by weight of $C_{1-12}$ alcohol.

3. The composition in claim 1, in which the composition contains water and an emulsifier, and is an aqueous emulsion.

4. A method of protecting the skin of a human being from ultraviolet radiation comprising applying to the skin an effective amount of the claim 1 composition.

* * * * *